United States Patent
Anderson et al.

(10) Patent No.: US 11,331,733 B2
(45) Date of Patent: May 17, 2022

(54) TOTAL CONTACT CAST SYSTEM AND METHODS FOR SAFE AND EASY REMOVAL THEREOF

(71) Applicant: WoundKair Concepts, Inc., Benbrook, TX (US)

(72) Inventors: Danny E. Anderson, Aledo, TX (US); Kimberly G. Anderson, Aledo, TX (US); Thomas E. Serena, Norwell, MA (US); Timothy A. Mayhugh, Erie, PA (US); James R. Wilcox, Jacksonville, FL (US); Cameron B. Morton, Madisonville, LA (US); Stephen C. Morvel, Jr., Aledo, TX (US)

(73) Assignee: Woundkair Concepts, Inc., Fort Worth, TX (US)

( * ) Notice: Subject to any disclaimer, the term of this patent is extended or adjusted under 35 U.S.C. 154(b) by 848 days.

(21) Appl. No.: 15/390,923

(22) Filed: Dec. 27, 2016

(65) Prior Publication Data

US 2018/0177642 A1 Jun. 28, 2018

(51) Int. Cl.
*A61F 15/02* (2006.01)
*B23D 57/00* (2006.01)
*A61F 13/04* (2006.01)

(52) U.S. Cl.
CPC .......... *B23D 57/0015* (2013.01); *A61F 13/04* (2013.01); *A61F 15/02* (2013.01)

(58) Field of Classification Search
CPC ..... A61F 15/02; A61F 13/04; B23D 57/0015; B26B 27/00; B26B 27/002
(Continued)

(56) References Cited

U.S. PATENT DOCUMENTS 2,878,806 A * 3/1959 French .................... A61F 15/02
602/9
3,150,470 A 9/1964 Barron
(Continued)

FOREIGN PATENT DOCUMENTS

DE 2901679 A1 12/1980
ES 2129340 A1 6/1999
(Continued)

OTHER PUBLICATIONS

Delaney, Lawrence A., M.D.; "An Improved Method of Cast Removal"; Orthopedic and Prosthetic Journal; 2 pages; Dec. 1965.
(Continued)

*Primary Examiner* — Camtu T Nguyen
(74) *Attorney, Agent, or Firm* — Whitaker Chalk Swindle & Schwartz PLLC; Charles Gunter (57) ABSTRACT

A cast system, which includes: a padding layer configured to be disposed within a cast and support a portion of a patient's limb; a casting material which hardens around the padding layer and form an outer shell of the cast surrounding the patient's limb; and a wire saw configured to be disposed within the cast and extend along a longitudinal axis of the cast. The wire saw has a cutting surface which is at least partly enclosed by a plastic sheath. By enclosing the wire saw cutting surface in a plastic sheath, the saw does not lock up during the cutting operation, cutting is facilitated, allowing for easy and safe removal of the cast by pulling at least one end of the wire saw so as to cut through the outer shell of the cast.

5 Claims, 6 Drawing Sheets

(58) Field of Classification Search
USPC .......................................................... 602/9
See application file for complete search history.

(56) References Cited

U.S. PATENT DOCUMENTS

| | | | | |
|---|---|---|---|---|
| 3,495,590 A * | 2/1970 | Warren | ................ | B23D 61/185 |
| | | | | 602/9 |
| 3,643,656 A * | 2/1972 | Young | .................... | A61F 13/04 |
| | | | | 602/13 |
| 3,998,219 A * | 12/1976 | Mercer | ................ | A61F 5/0585 |
| | | | | 602/6 |
| 4,019,506 A * | 4/1977 | Eschmann | .............. | B32B 5/028 |
| | | | | 602/8 |
| 4,041,941 A * | 8/1977 | Driver | .................... | A61F 15/02 |
| | | | | 602/9 |
| 4,290,424 A | 9/1981 | Wahl et al. | | |
| 4,685,453 A * | 8/1987 | Guignard | ................ | A61L 15/07 |
| | | | | 602/7 |
| 4,709,699 A | 12/1987 | Michael et al. | | |
| 4,829,993 A * | 5/1989 | Silvey | .................... | A61F 13/041 |
| | | | | 602/9 |
| 4,888,225 A * | 12/1989 | Sandvig | ............... | A43D 999/00 |
| | | | | 428/71 |
| 5,944,675 A * | 8/1999 | Bequet-Sharber | ...... | A61F 15/02 |
| | | | | 602/9 |
| 6,974,431 B2 * | 12/2005 | Jensen | .................... | A61F 13/04 |
| | | | | 128/882 |
| 2008/0287852 A1 * | 11/2008 | Evans | .................... | D04B 21/18 |
| | | | | 602/43 |
| 2012/0265113 A1 * | 10/2012 | Crago | .................... | A61F 15/006 |
| | | | | 602/27 |
| 2013/0172796 A1 * | 7/2013 | Oladipo | .................. | A61F 15/02 |
| | | | | 602/9 |
| 2017/0239097 A1 * | 8/2017 | Serena | .................. | A61F 5/0111 |

FOREIGN PATENT DOCUMENTS

GB      2 003391 A  *  3/1979
GB      2003391 A       3/1979

OTHER PUBLICATIONS

Boneguard "CastBuster" Brochure; 7 pages; Boneguard, Inc.; Canton, MA.; copyright 2009-2016; www.boneguardcasting.com.

\* cited by examiner

TOTAL CONTACT CAST SYSTEM AND METHODS FOR SAFE AND EASY REMOVAL THEREOF

BACKGROUND

1. Field of the Invention

The present invention relates generally to an improved cast system, particularly to a total contact cast system, that provides for fast, easy, and safe removal of a total contact cast from a patient's body.

2. Description of the Prior Art

Many people suffer from ulcerations, sores, and other types of wounds in one or more appendages, particularly in the feet. For example, people suffering from diabetes also frequently suffer from poor blood circulation in their appendages and, as a result, are at higher risk of developing sores, wounds, or ulcers on their feet. While diabetic foot ulcers account for the majority of neuropathic ulcers on the foot, blockage of arteries supplying blood to the foot, malignancies, venous insufficiency, rheumatoid arthritis and other medical conditions can also cause such ulcers. Due to their location, diabetic and neuropathic foot ulcerations can be quite challenging to heal.

Various types of casts and boots have been developed to treat individuals suffering from diabetic or neuropathic foot wounds. Total Contact Casting was first introduced to the United States over 70 years ago from the leper colonies of India, and has since proven to be particularly efficacious for the treatment of diabetic and neuropathic foot ulcerations. As described by the name, a "total contact cast" is meant to fit the patient's leg and foot very closely, and to touch or be in contact with the patient's whole foot. This intimate contact is designed to secure the foot and leg in a position that allows the patient to ambulate while not allowing the foot to move in the east, thereby removing pressure from the wound. The initial cast is usually reapplied within 4 to 72 hours after application to accommodate any reduction of swelling and edema in the leg/foot, which is typically followed by a weekly removal and reapplication (changing) of the cast.

The total contact cast typically has a hard outer shell (usually made of plaster or fiberglass), usually applied in several layers, and a soft cast padding (such as gauze, pre-formed cast padding, a stockinet, and/or a compression sock) underneath the outer shell. The purpose of the hard outer shell is to immobilize and protect the patient's particular body part, whereas the purpose of the padding is to provide a comfortable interface between the outer shell and the patient's skin and to protect the patient from injury during removal of the cast by a cast saw. However, during removal of the cast by cutting with a cast saw, it is not uncommon for more pressure than is necessary to be applied to the cast saw, resulting in the oscillating blade penetrating the cast padding and potentially cutting or burning the patient's skin below.

The removal of total contact casting has been a long-standing issue. Prior total contact casting systems had to be spread open at the center while supporting the patient's leg with opposing pressure until the cast broke. This method requires significant strength and can be very time consuming. On the other hand, using a cast saw to facilitate cast removal requires operation by a skilled operator and poses the inherent risk of accidental injury to the patient.

Where a traditional cast saw is used to cut through fiberglass cast materials, a good deal of dust is created which can create a hazardous environment for health care workers in the vicinity of the cast removal operation, some of whom may remove twenty to thirty casts a day, or more.

A variety of products and approaches have been utilized in attempting to avoid cutting or burning a patient during cast removal, but with little success. As a result, despite the clinical effectiveness of total contact casting for the treatment of neuropathic and diabetic foot ulcerations, conventional removal methods pose a significant problem, resulting in less than 3% of clinicians currently utilizing total contact casting to treat their diabetic and neuropathic foot ulcer patients.

SUMMARY OF THE INVENTION

It is an object of this invention to overcome the challenges encountered during removal of cast and particularly of total contact casts. In particular, it is an object of the invention to provide a means for quicker and easier cast removal, while protecting a patient's skin during the process.

The method of the invention substitutes a "cutting wire" or "wire saw" for the traditional Stryker® style power cutting saw which has been used in the past. The terms "cutting wire" and "wire saw" are used interchangeably in the discussion which follows.

In one aspect of the invention, a casting system is provided comprising: a padding layer configured to be disposed within the cast and support a portion of a patient's limb; a casting material configured to harden around the padding layer and form an outer shell of the cast surrounding the patient's limb; and a cutting wire or cutting saw configured to be disposed within the cast and extend along a longitudinal axis of the cast. The wire saw is a flexible metal cutting wire or cable, optionally serrated, and configured to cut through the outer shell of the cast when a pulling force is applied by pulling at least one end of the wire towards the other end. The cutting wire is enclosed in a plastic sheath.

In some cases, the padding layer may be one or more (e.g., multiple) padding layers. The casting material may be a hardening material selected from the group consisting of fiberglass, carbon fiber, thermoplastic, bandaging, casting tape, coated fabrics, and combinations thereof. In certain embodiments, the casting material is configured to begin hardening and form the outer shell upon exposure to air and/or water. A thickness of the outer shell formed by the casting material may typically range from about 1 mm to 4 cm.

In one particularly preferred form of the invention, a novel cutting assembly is provided for removing a cast from a limb of a patient's body. The cutting assembly includes a wire saw of a given length which defines a cutting surface between two opposing ends thereof, the ends terminating in attachment points for attaching gripping members. One suitable type of wire saw is a metal wire or cable which uses abrasion for cutting rather than saw teeth. A plastic sheath encloses and contains at least a portion of the cutting surface of the wire saw. Preferably, the entire cutting surface is enclosed. The plastic sheath with its contained wire saw are of a selected length which allows the sheath and wire saw to be installed within a cast, whereby the plastic sheath is at least partly covered by the cast materials as the cast is applied to the patient's body and then allowed to cure. Preferably, all but the two opposing ends of the plastic sheath and wire saw are covered by the cast materials. There are also preferably two wire saws in their sheaths which are applied along opposite sides of the patient's limb. The cured cast is subsequently removable from the patient's body by sawing the cast materials with the wire saw while the saw is contained in the plastic sheath. Sawing is facilitated by attaching gripping members to the respective opposing ends of the wire saw and by pulling on at least one of the respective ends of the wire saw to cut through the cast materials. The plastic sheath prevents the wire saw from becoming stuck in the cast materials being cut and locking up during the cutting process.

In one preferred form, the plastic sheath has a front sidewall and a rear sidewall, the rear sidewall being provided with a peel-off adhesive strip, so that the plastic sheath can be made to adhere to underlying cast materials as the cast materials are being applied to the patient's limb. The front sidewall of the plastic sheath can be transparent so that the wire saw is visible in its packaging.

The cast system described herein may be a total contact cast and configured to receive a portion of a patient's anatomy, for example, a portion of the patient's lower leg. Where the cast system is a total contact foot cast, the cast may additionally include a suitable foot base configured to attach to a bottom surface of the cast to allow the patient to walk on the cast.

A method is shown herein for applying the previously described total contact cast to a patient's lower leg. In the method of the invention, a padding layer is applied to at least a portion of the patient's lower leg. The cutting wire and associated sheath are positioned so as to run parallel to the length of the cast along a longitudinal axis thereof. One or more layers of the casting material are then applied over the cutting wire contained within the associated sheath and over the padding layer.

A method is also shown for removing the previously described total contact cast from a patient's lower leg. The cast is removed by pulling on the opposing ends of the wire saw in a back-and-forth direction so as to cut through the casting material forming an outer shell of the cast. Again, the sawing method can be facilitated by attaching a handle attachment to an attachment point provided on the wire saw and pulling the wire saw wire with the handle attachment so that that the wire saw cuts through the outer shell of the cast.

Methods encompassed by the invention may additionally include applying any suitable and known or novel wound dressing to a wound prior to application of a padding layer and/or orthopedic sock and the casting material. The method may also encompass treating a neuropathic foot wound of a patient, the method comprising: applying dressing to the foot wound of the patient; covering the lower leg of the patient with a sock; and applying the previously described total contact cast around the patient's lower leg. The cast may be subsequently removed by pulling at least one end of the previously described wire saw in a direction of the other end so as to cut through the casting material forming the outer shell of the cast.

Additional objects, features and advantages will be apparent in the written description which follows.

DETAILED DESCRIPTION OF THE INVENTION

The present disclosure describes for the first time a casting system that is easily and safely removable by medical personnel. Specifically, the casting system with its "cutting wire" or "wire saw" and associated plastic containment sheath, as well as the methods described below, allow medical personnel to freely cut through the outer shell of the cast during cast removal without the risk of burning or cutting the patient's skin underneath.

The present invention may be understood more readily by reference to the following detailed description of the preferred embodiments of the invention. However, before the casting system, cast, different components and methods are disclosed and described, it is to be understood that this invention is not limited to specific cast types, assemblies or configurations, specific conditions, or specific methods, as such may vary, and any modifications thereto and variations therein will be apparent to those skilled in the art. It is also to be understood that the terminology used herein is for the purpose of describing specific embodiments only and is not intended to be limiting.

As has been mentioned, the terms "cutting wire" and "wire saw" are used interchangeably in this discussion and will be taken to mean a flexible wire or cable, optionally serrated, which uses abrasion to cut, rather than saw teeth. Depending on the application, diamond material may or may not be used as an abrasive. The wire can have one strand or many strands braided together (cable). A single-strand saw can be roughened to be abrasive, abrasive compounds can be bonded to the cable, or diamond-impregnated beads (and spacers) can be threaded on the cable. One major advantage of wire saws is their smaller kerf, as compared to a blade. Another is the precision of the cut. They also do not create dust when cutting fiberglass type cast materials, as did the prior art power saws or cutting tools. Thus, instead of using a blade, a cutting wire typically uses wire of various diameters and lengths, impregnated with diamond dust of various sizes to cut through materials. Because of the hardness of diamonds, this cutting technique can cut through almost any material that is softer than the diamond abrasive. Diamond cutting wire is also more practical and less expensive than some other cutting techniques.

As used herein, "lower leg" may refer to any portion of a patient's leg that is located distal to the patient's knee and including the patient's foot.

As used herein, the terms "patient" and "individual" refer to any person or other subject that can wear or use the described cast system. In certain embodiments, the patient is a person suffering from a diabetic or neuropathic ulceration, sore, or other type of wound in an appendage (e.g., lower leg).

The Cutting Assembly:

The cutting assembly of the invention which is used for removing a cast from a limb of a patient's body will now be described. The cutting assembly includes a wire saw of the type previously described, having a given length which defines a cutting surface between two opposing ends thereof, the ends terminating in attachment points for attaching gripping members. A particular type of plastic sheath encloses and contains at least a portion of the cutting surface of the wire saw. The plastic sheath and contained wire saw are of a selected length which allows the sheath and wire saw to be installed within a cast, whereby the plastic sheath is at least partly covered by the cast materials as the cast is applied to the patient's body and then allowed to cure. The cured cast is subsequently removable from the patient's body by sawing the cast materials with the wire saw while the saw is contained in the plastic sheath.

As briefly described, the cutting wire (11 in FIG. 10) used in the practice of the invention may be any conventional or novel cutting wire or wire saw, including (but not limited to) spiral and serrated cutting wires. The cutting wire may be of any suitable material, including, but not limited to, metals (solid or tipped), such as steel, hardened steel, stainless steel, titanium, titanium alloys, tungsten carbide, brass, and/or cobalt. Preferably, the cutting wire is a diamond cutting wire where the wire is impregnated with diamond dust. Such cutting wires are commercially available from a number of sources and will be familiar to those skilled in the cutting arts where they are normally employed. The cutting wire may be of a length substantially corresponding to the longitudinal length of the cast in which it is employed. Moreover, the cutting wire is preferably positioned so as to run along a longitudinal axis of the cast in which it employed.

In addition to the wire saw 11, the cutting assembly of the invention includes an associated plastic containment sheath (29 in FIG. 10) which encloses and contains at least a portion of the cutting surface of the wire saw. Preferably, the plastic sheath encloses the entire wire saw, as illustrated in FIG. 10.

Figure 1:
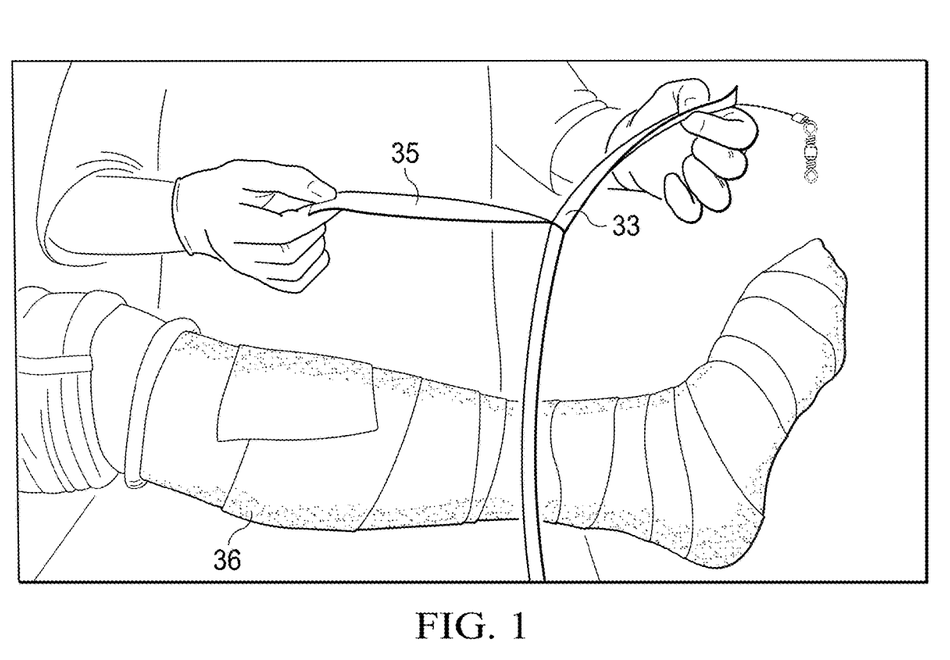
FIGS. 1-5 illustrate the various steps in the method of applying the cast and cutting assembly of the invention, in this case in a total contact cast system.
Figure 2:
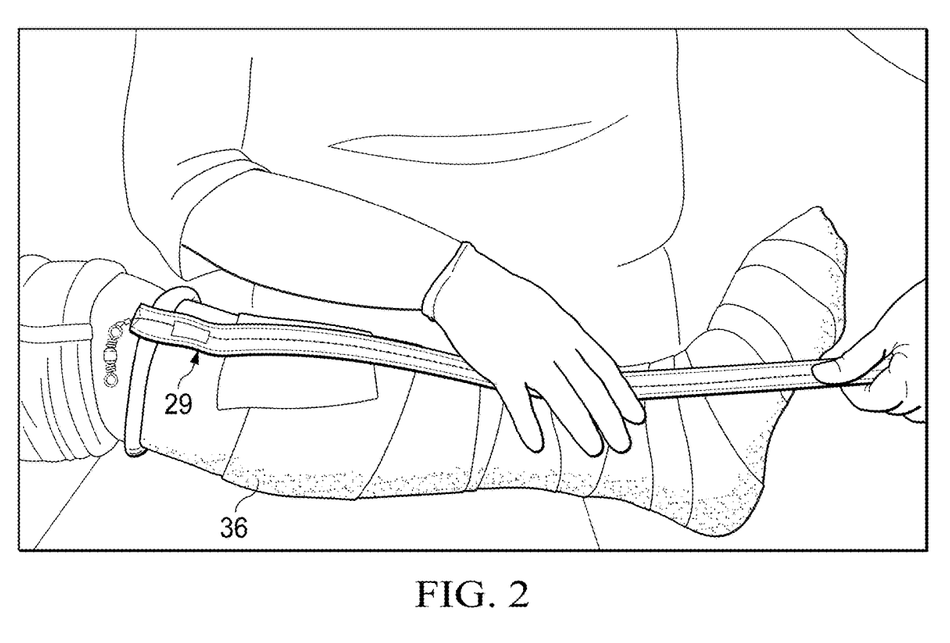
Figure 10:
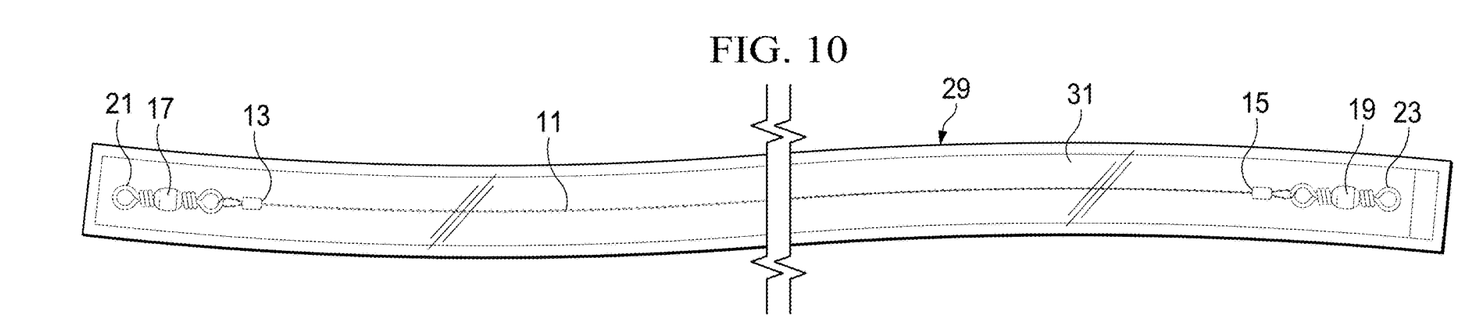
FIG. 10 is a top view of the cutting wire and containment sheath of the invention, partly broken for ease of illustration.

As shown in FIGS. 1, 2 and 10, the plastic sheath is a planar "envelope" that has a front sidewall (31 in FIG. 10) and a rear sidewall (33 in FIG. 1). The rear sidewall 33 is provided with a peel-off adhesive backing strip (35 in FIG. 1), so that the plastic sheath can be made to adhere to underlying cast materials as the cast is being applied to the patient's limb. FIGS. 1 and 2 illustrate a medical worker peeling off the backing strip 35 and then applying the plastic sheath 29 down the length of the padding material 36 covering the patient's lower limb.

In the case of the plastic sheath of FIG. 10, the front and rear sidewalls 31,33, of the plastic sheath form an "envelope" which is approximately 3 mils thick. The front sidewall 31 is transparent plastic. In one exemplary embodiment of the invention, the front and rear sidewalls of the plastic sheath form a flexible package much like a packaging list envelope used in mailing and shipping applications. In other words, shipping indicia, such as a packing slip, would be inserted within the "envelope" and would be visible through the transparent front sidewall once the rear adhesive backing strip is removed and the envelope is adhered to the front of a package being shipped. In the example shown, the total plastic packaging is approximately 3 mils thick and approximately 1.75 inches wide by 27 inches long. A Super Stick® adhesive is applied to the rear exposed sidewall and initially covered by the removable, peel-off backing strip.

Figure 3:
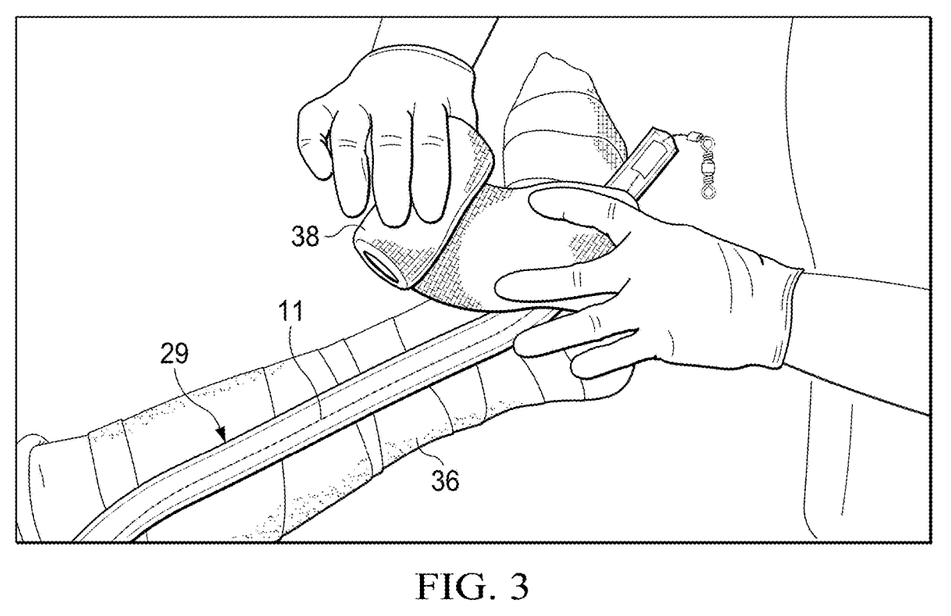
Figure 4:
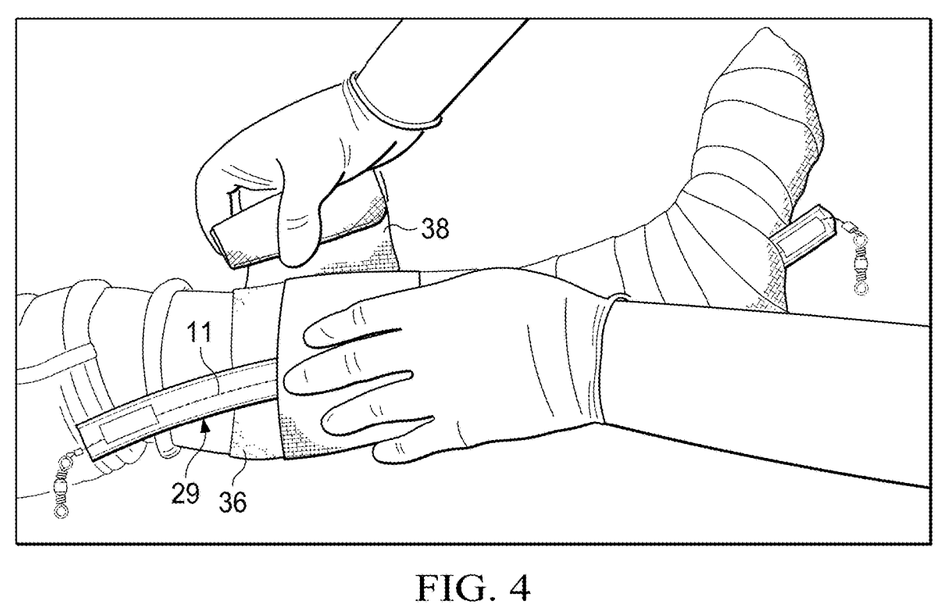
Figure 5:
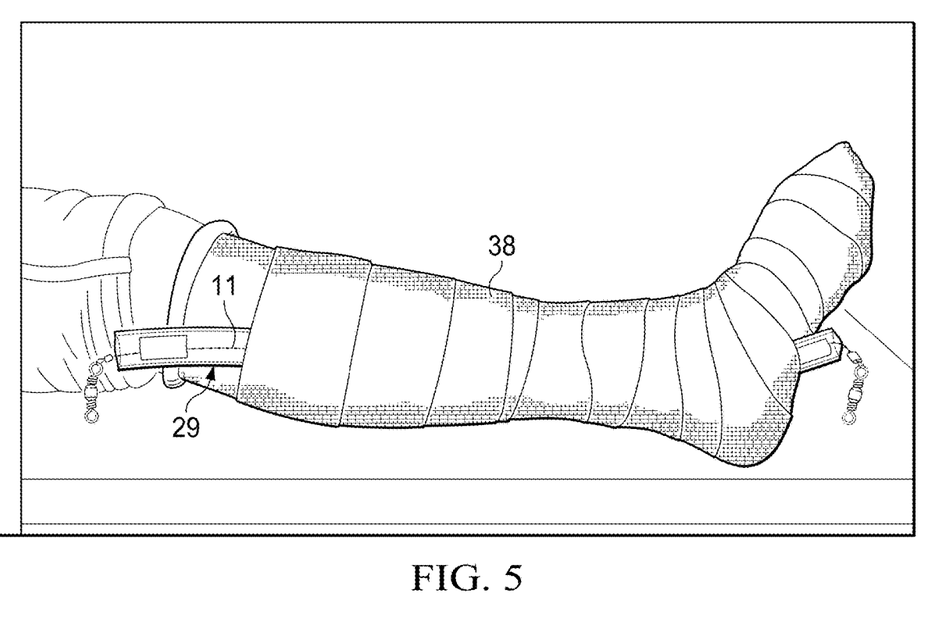

As will be evident from FIGS. 1-5, the plastic sheath 29 and contained wire saw 11 are of a selected length which allows the sheath and wire saw to be installed within a cast, whereby the plastic sheath is at least partly covered by the cast materials as the cast is applied to the patient's body and then allowed to cure. In other words, the plastic sheath 29 and wire saw 11 are applied to the cast padding (shown as 36 in FIGS. 1 and 2), and the additional cast materials 38 are wound about the patient's lower leg (as shown in FIGS. 3 and 4), FIG. 5 shows the plastic sheath 29 extending from the opposite ends of the total contact cast.

Figure 6:
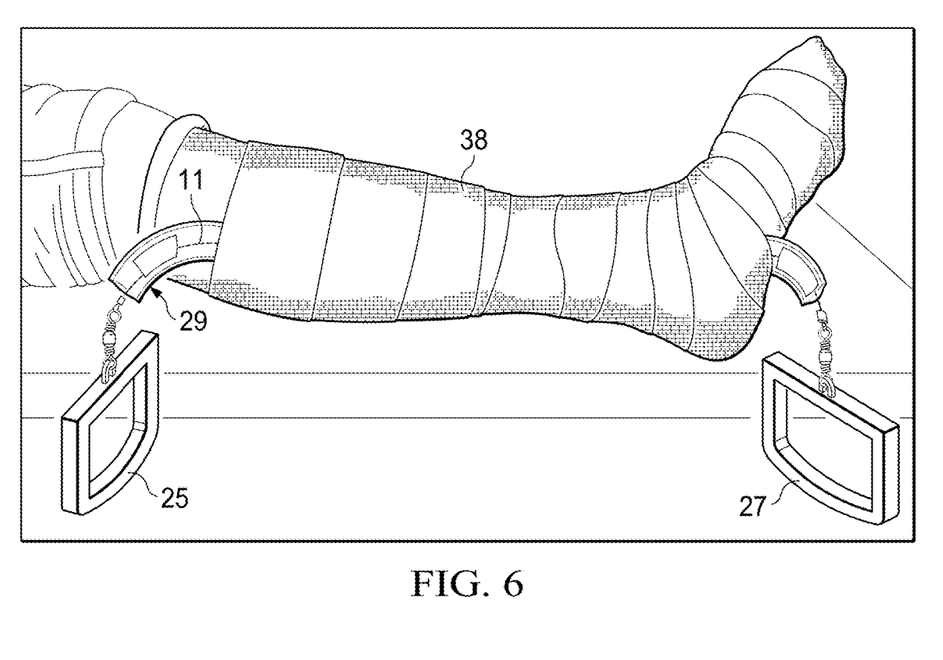
FIG. 6 illustrates an exemplified handle attachment for the cutting wire employed in the method of the invention.
Figure 7:
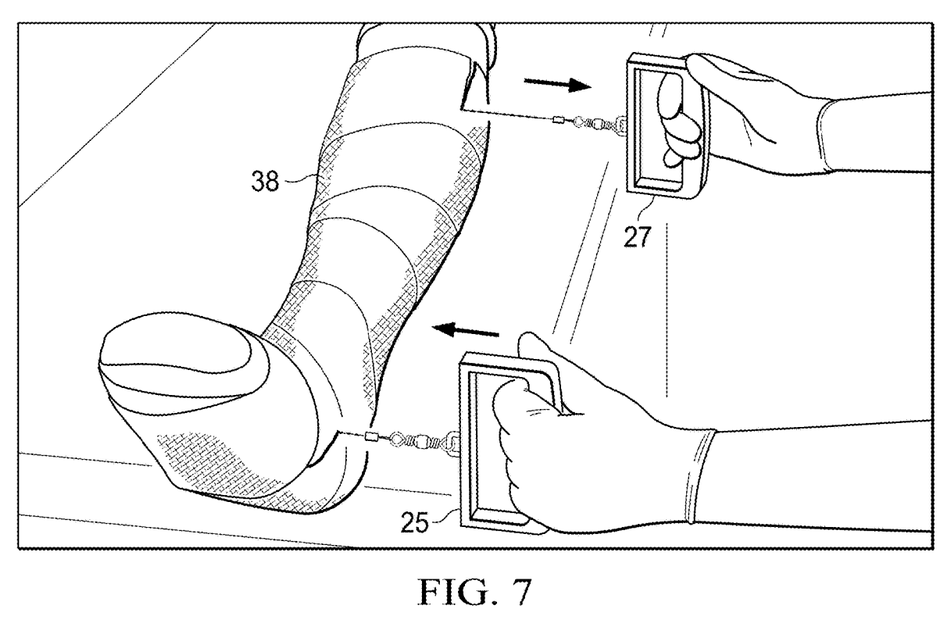
FIGS. 7-9 illustrate the cast removal process of the invention using the novel cutting wire and containment sheath.
Figure 8:
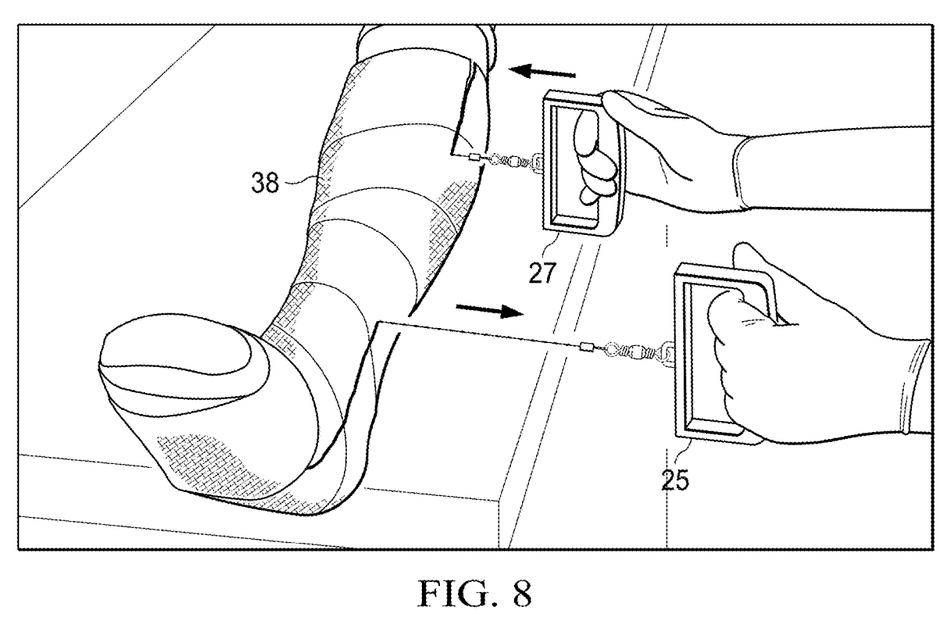

Once the cast has cured and hardened, the exposed opposing ends of the plastic sheath and wire saw (shown in FIG. 5) may be temporarily concealed, for example, by turning them in and covering them with a cloth sock until it is time to remove the cast. As shown in FIGS. 6-8, the cured cast is subsequently removable from the patient's body by sawing the cast materials with the wire saw 11 while the saw is contained in the plastic sheath 29. FIG. 6 shows the attachment handles 25, 27, attached to the attachment points on the opposite ends of the wire saw, ready to be used in the sawing operation.

Figure 11A:
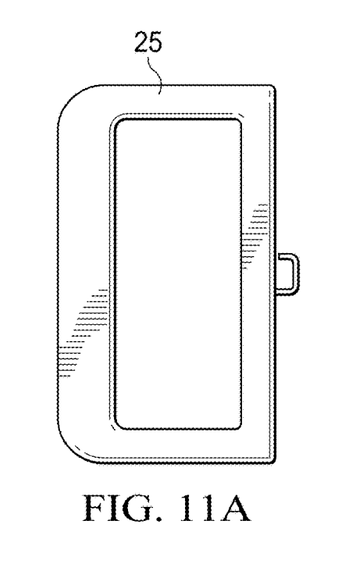
FIGS. 11A and 11B are isolated views of the two attachment handles used with the cutting wire of the invention.
Figure 11B:
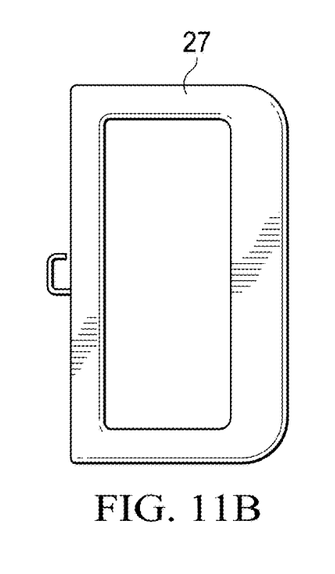

As perhaps best seen in FIG. 10, the wire saw (1.1 in FIG. 10) is of a selected length which defines a cutting surface between two opposing ends 13, 15, thereof, the ends terminating in attachment points 17, 19, for attaching gripping members. In the case of the cutting saw of FIG. 10, the attachment points 17, 19, comprise swivel attachments having end loops 21, 23. The end loops 21, 23, are engageable with gripping members (25, 27 in FIGS. 11A and 11B) during the cast removal process. Suitable handle attachments include, for example, such things as a molded handle that may hook or attach to the attachment points; a ring; or a chord, such as a parachute chord that may be attached/tied to the attachment points.

Figure 9:
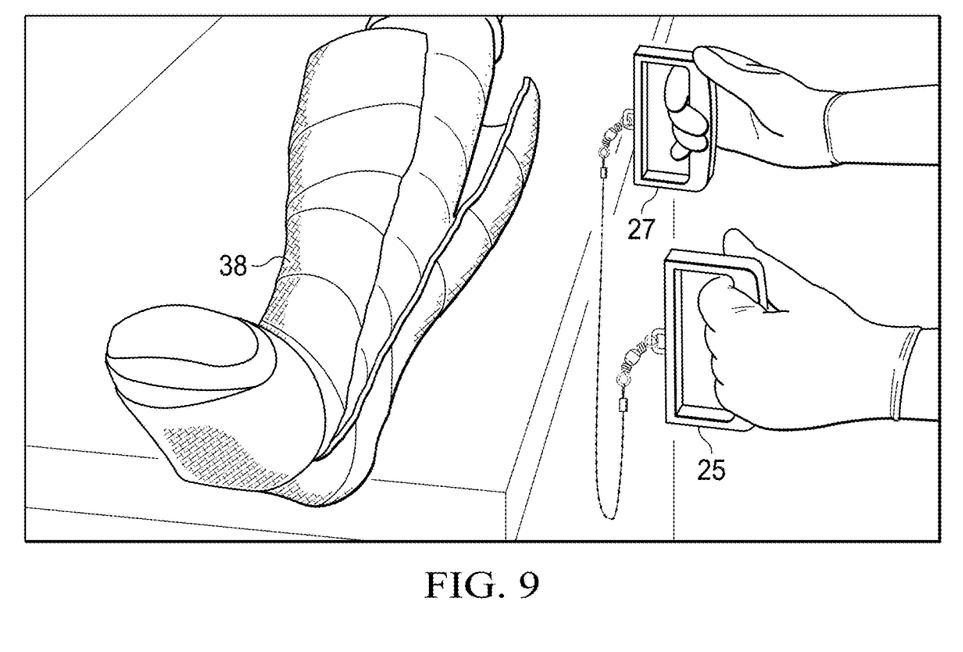
Figure 9A:
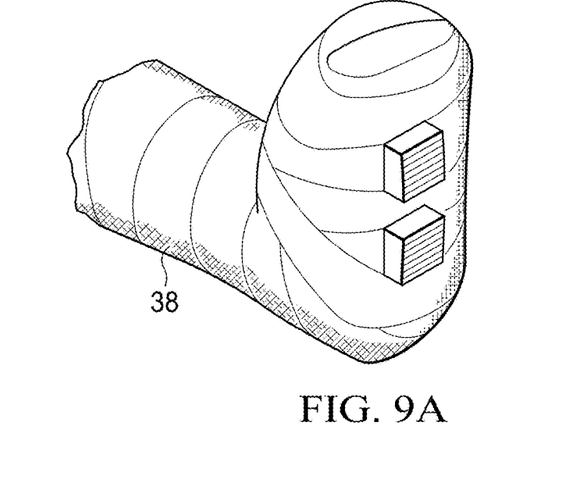
FIG. 9A shows a walking heel installed as a part of the total cast system of the invention.

FIGS. 7 and 8 illustrate the beginning stages of the sawing operation where a medical worker pulls back and forth on the handles 25, 27 to cut a longitudinal slit in the cast material. FIG. 9 shows the cast having been cut along one side. It will be understood that normally a cutting wire and sheath would be installed on both sides of the cast. In this case, only one wire saw and sheath are shown for ease of illustration and to not further complicate the view.

Thus, as has been described, the wire saw 11 is ultimately positioned within the cast (see FIGS. 1-5) between the patient's skin (optionally covered by a compression sock) and the casting material, such as, e.g., between the padding layer and the casting material. As shown in FIGS. 1-5, the cast may be configured so as to extend over a first surface of a patient's appendage (e.g., lower leg), over an end of the appendage (e.g., foot), and over a second surface of the appendage, which is substantially opposite to the first surface. For example, the cast may be configured so as to extend: over a posterior portion of a patient's lower leg (e.g., calf), over the patient's heel, across a length of the sole of the patient's foot, over an anterior portion of the foot (e.g., toes), across a dorsal portion of the foot; and over an anterior portion of the lower leg (e.g., shin). As described with respect to FIGS. 1 and 2, the cast may be a foot cast (e.g., total contact cast) which includes a padding layer positioned between the patient's skin (optionally covered by a compression sock and the casting material. As shown in FIG. 2, the cutting wire and its associated plastic containment sheath may be positioned along a longitudinal axis of the cast, e.g., along a central portion of the cast, along a posterior side of the cast, or along an anterior side of the cast.

While the cutting assembly of the invention can be used with a variety of cast systems, the preferred total contact cast system will now be described. This cast system includes a padding layer configured to be disposed within the cast and support a portion of a patient's limb and a casting material configured to harden around the padding layer and form an outer shell of the cast surrounding the patient's limb.

The Casting System:

It will be appreciated that, while the referenced cast is described herein for use as a total contact cast for treatment of ulcerations, sores, and/or any other wounds on a foot, the cast can easily be modified to be used for any other suitable purpose. For example, it is envisioned that the cast can be used for protecting an appendage with a broken and/or fractured bone while the bone heals, and/or for immobilizing or restricting access to an appendage. It is furthermore envisioned that the cast can be configured to, e.g., extend up a patient's leg and past the knee. Accordingly, in certain embodiments of the invention, the cast (not shown) is configured to extend over one or more appendages of a patient, such as the patient's arm, finger, and/or torso. In such embodiments, the cast may be configured to, e.g., extend over a posterior portion of a patient's forearm, wrap over a distal end of the patient's hand (e.g., over the distal end of the patient's fingers and/or with one or more of the patient's fingers extending through a corresponding hole or holes in the casting material), or extend over an anterior portion of the patient's forearm.

The various components of the total contact cast system described herein can be used in any suitable manner that allows the components (individually or in combination) to help protect a wounded portion of a patient's limb, while allowing for easy and safe removal of the cast when necessary. The various components of the described cast system can be used in any suitable combination, meaning that portions of the cast system can be omitted and/or replaced with one or more known or novel components, and any additional components (such as, e.g., wound dressing, casting material, boot, footplate, shoe, ointment, etc.) can be added or used with one or more components of the described cast system.

The Casting Material:

The cast described herein can comprise any suitable casting material that allows the cast to substantially conform to the shape of a patient's appendage (e.g., lower leg) during application and then harden in that shape to form a rigid cast. Examples of suitable casting materials include (but are not limited to) any known or novel: fiberglass casting material (e.g., fiberglass that has been impregnated with polyurethane and/or another suitable material, fiberglass that is coated with and/or otherwise comprises silver, copper, nickel, iodine, bamboo, and/or another suitable antimicrobial material and/or anti-odor material, and/or combinations thereof); hardenable bandaging (e.g., cotton bandaging that is coated with plaster, polyester bandaging that is covered with plaster, and/or any other suitable bandaging material that is configured to harden after application); a thermoplastic casting material; a polypropylene casting material; a carbon fiber casting material; a hardenable antimicrobial material, such as, e.g., a plaster or another suitable hardenable material covering a bamboo cloth, a bamboo rayon, a polyester made from bamboo, other types of fabric comprising bamboo, and/or a silver-coated fabric (e.g., silver coated polyethylene terephthalate, silver-coated rayon, silver-coated polyester, etc.), a copper-coated fabric, a silver/copper-coated fabric, a silver/copper/nickel-coated fabric, a silver/copper/tin-coated fabric, an iodine incorporated cloth, and/or any other suitable material having one or more antimicrobial and/or anti-odor features; a casting material (e.g., fiberglass, cotton bandaging, and/or any other suitable casting material) that is impregnated with and/or otherwise comprises a suitable antibiotic, bactericide, and/or other antimicrobial ingredient (e.g., penicillin, amikacin, gentamicin, kanamycin, netimicin, tobramycin, streptomycin, spectinomycin, geldanamycin, herbimycin, rifaximin, ertapenem, doripenem, imipenem, meropenem, defadroxil, cefazolin, cefalotin, cephalexin, and/or any other suitable antimicrobial); casting tape; and/or any other suitable material that is configured to be formed around a portion of a patient's limb and then hardened to form a rigid cast. In one preferred form, the outer shell 38 is a fiberglass material that begins hardening once it is exposed to air and/or water.

As has been briefly described, the cast can comprise any suitable number of layers of casting material. For example, the cast of the invention may comprise between 1 and 20 layers of casting material, including any suitable number of layers of casting material that fall within the aforementioned range, such as, e.g., between 5 and 10 layers. The casting material can also have any suitable thickness, such as between 1 mm and about 4 cm.

The casting material may be in the form of a plurality of strips or a single strip configured to form an outer shell of the cast on an appendage (e.g., lower leg). The strips can have any suitable shape, such as, e.g., rectangular, belt-shaped, triangular, rounded, polygonal, irregular, symmetrical, asymmetrical, ribbon-like, cord-like, rope-like, and/or any other suitable shape. The casting material may furthermore be of any desired length or lengths (if a plurality of strips are to be applied) to form an outer shell of the cast of the desired thickness and covering the desired body part. For example, some of the strips may be configured to circumscribe a portion of the cast, some of the strips may be configured to extend only partially around a part of the cast, or some of the strips may be configured to overlap with each other. While the strips can run substantially perpendicular to a length (or a longitudinal axis) of the cast, the straps may also, or alternatively, be configured to run at an angle with respect to the length (or a longitudinal axis) of the cast.

The Padding Layer:

With respect to the padding layer, the cast of the invention may include any suitable amount or layers of padding in any suitable location (e.g., over a patient's toes, dorsal portion of the patient's foot, shin, calf, ankle, a lateral side of a person's lower leg, or any other body part to be cast that could benefit from additional padding. The aforementioned padding can be modified in any suitable manner that allows it to pad, provide shear reduction to, ventilate, and/or otherwise protect an appendage within a cast (e.g., cast). In certain embodiments, additional support, protection, and/or padding may be provided in the form of a sock, such as a compression sock.

Where the cast comprises a padding layer, any suitable type of padding material may be used, including (but not limited to) closed cell padding, open cell padding, polymer padding (e.g., polypropylene, polyethylene, polyurethane, etc.), foam, silicon, gel, cotton, vinyl, polyvinyl chloride, ethylene vinyl acetate, cork, and/or combinations thereof. Although some embodiments of the cast system comprise a single type or layer of padding material, in other embodiments, the cast system comprises a plurality of types and/or layers of padding material.

In certain embodiments, the padding layer may be attached to a portion of any suitable type of sock (e.g., a compression sock) or other material directly disposed over the patient's body part (e.g., lower leg, hand, arm, etc.). The padding layer may be configured and applied to the patient's body part so as to move completely independently of the outer shell of the cast formed by the casting material. Alternatively, one or more of the padding layers may be at least partially attached to the casting material when the cast is disposed on the body part. As a result of the latter embodiment, the described padding layer is able to reduce shearing forces between the casting material and the patient's skin.

Suitable materials for assembling the casting system of the invention are commercially available from WoundKair Concepts, of Fort Worth, Tex., as the TrueKAST™ Total Contact Casting System.

An invention has been provided with several advantages. The cutting assembly of the invention provides a method for easily and safely removing a cast from a portion of a patient's anatomy, such as the patient's limb (e.g., lower leg). In one aspect, the present invention provides a method of cutting such a hardened cast by pulling on the cutting wire embedded in or under the hardened outer shell of the cast in a distal or proximal direction (at the discretion of the user or medical personnel), thereby cutting through the casting material forming the hardened outer shell without the need for scissors or oscillating cutting saws. The danger of inadvertently cutting the patient is removed. There is no danger of burning the patient's skin during the cutting operation. Also, the use of a wire saw eliminated the dust which is created in the surrounding environment when, for example, cutting fiberglass with a power saw.

While the invention has been shown in only one of its forms, it is not thus limited but is susceptible to various changes and modifications without departing from the spirit thereof.

What is claimed is:

1. A method of applying and removing a total contact cast, the method comprising the steps of:
   applying a padding layer to a lower leg region of a patient's body;
   securing a sheathed wire saw to the padding layer, wherein the sheathed wire saw includes:
      a flexible plastic sheath which encloses a flexible metal cutting wire having a selected length which defines a cutting surface between two opposing ends thereof, the two opposing ends terminating in attachment points, comprising swivel attachments, for attaching gripping members, the selected length of the flexible metal cutting wire defining a cutting surface extending the entire selected length between the two attachment points;
      the sheathed wire saw being supplied as an assembly with the flexible plastic sheath enclosing the entire cutting surface of the flexible metal cutting wire, the flexible plastic sheath being a planar envelope having a front sidewall and a rear sidewall and having an opening which receives the cutting surface of the flexible metal cutting wire, wherein the flexible metal cutting wire is free to move within the flexible plastic sheath;
      wherein the rear sidewall of the flexible plastic sheath has attached thereto a peel-off adhesive strip to facilitate attachment of the sheathed wire saw to the padding layer;
   applying a casting material over the sheathed wire saw and over the padding layer to form an outer shell of a total contact cast;
   allowing the casting material to cure with the flexible metal cutting wire being enclosed in the flexible plastic sheath at the time the casting material is being applied, so that the casting material cures around and over the enclosed flexible metal cutting wire; and
   subsequently removing the casting material by attaching handle attachments to the attachment points provided on the flexible metal cutting wire and pulling with the handle attachments so that the flexible metal cutting wire cuts through the outer shell of the total contact cast.

2. The method of claim 1, wherein the padding layer comprises multiple padding layers.

3. The method of claim 2, wherein the casting material is a hardening material selected from the group consisting of fiberglass, carbon fiber, thermoplastic, bandaging, casting tape, coated fabrics, and combinations thereof.

4. The method of claim 1, wherein the flexible plastic sheath is 3 mils thick.

5. A method of treating a neuropathic foot wound of a patient, the method comprising the steps of:
   covering a lower leg of the patient with a sock;
   covering the sock and the lower leg of the patient with a padding layer;
   applying a total contact cast including a casting material configured to harden around the padding layer and form an outer shell around the patient's lower leg and the padding layer and subsequently removing the total contact cast, the method further comprising the steps of:
   securing a sheathed wire saw to the padding layer prior to applying the casting material, wherein the sheathed wire saw comprises:
      a flexible plastic sheath which encloses a flexible metal cutting wire having a selected length which defines a cutting surface between two opposing ends thereof, the two opposing ends terminating in attachment points, comprising swivel attachments, for attaching handle attachments, the selected length of the flexible metal cutting wire defining a cutting surface extending the entire selected length between the two attachment points;
      the sheathed wire saw being supplied as an assembly with the flexible plastic sheath enclosing the entire cutting surface of the flexible metal cutting wire, the flexible plastic sheath being a planar envelope having a front sidewall and a rear sidewall and having an opening which receives the cutting surface of the flexible metal cutting wire, wherein the flexible metal cutting wire is free to move within the plastic sheath;
      wherein the rear sidewall of the flexible plastic sheath has attached thereto a peel-off adhesive strip to facilitate attachment of the sheathed wire saw to the padding layer;
   allowing the casting material to cure with the flexible metal cutting wire being enclosed in the flexible plastic sheath, so that the casting material cures around and over the enclosed flexible metal cutting wire;
   subsequently removing the casting material by attaching handle attachments to the attachment points provided on the flexible metal cutting wire and pulling with the handle attachments so that the flexible metal cutting wire cuts through the outer shell of the total contact cast; and
   wherein the flexible plastic sheath forms an envelope which is approximately 3 mils thick.

* * * * *